Figure 1:
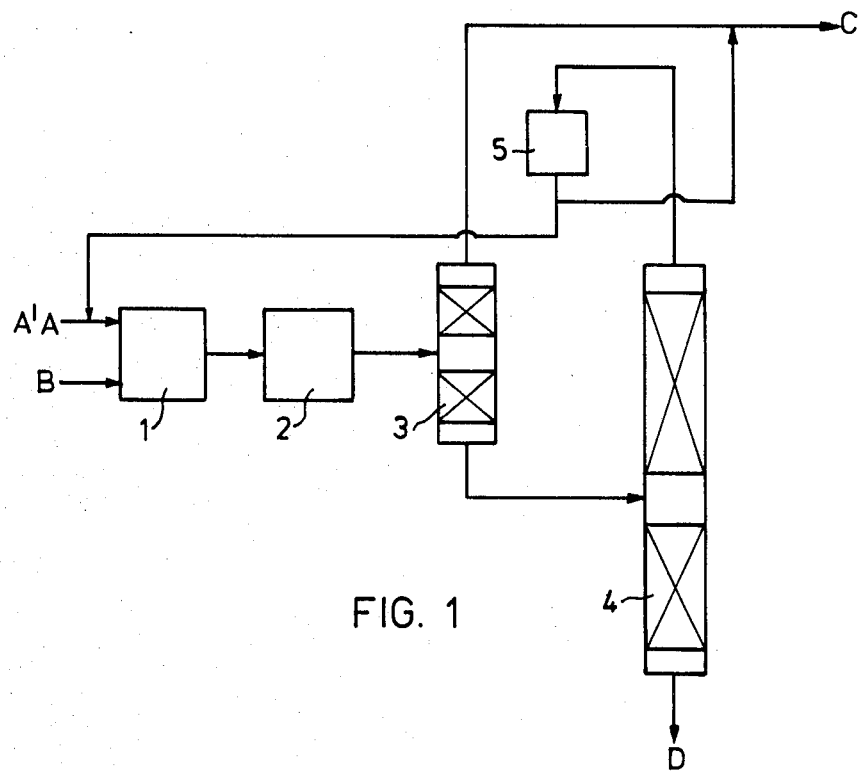

United States Patent [19]

Schmidt et al.

[11] 4,296,047
[45] Oct. 20, 1981

[54] CONTINUOUS PREPARATION OF PHOSPHORIC ACID ALKYL ESTER DICHLORIDES

[75] Inventors: Karl-Julius Schmidt; Friedrich Schmidt, both of Wuppertal; Peter Siegle, Cologne, all of Fed. Rep. of Germany; Gert Hansen, Sao Paulo, Brazil

[73] Assignee: Bayer Aktiengesellschaft, Leverkusen, Fed. Rep. of Germany

[21] Appl. No.: 129,852

[22] Filed: Mar. 12, 1980

[30] Foreign Application Priority Data

Mar. 24, 1979 [DE] Fed. Rep. of Germany ....... 2911700

[51] Int. Cl.$^3$ .............................................. C07F 9/14
[52] U.S. Cl. ................................................. 260/974
[58] Field of Search ........................................ 260/974

[56] References Cited

U.S. PATENT DOCUMENTS

| | | | |
|---|---|---|---|
| 1,945,183 | 1/1934 | Clemmensen | 260/974 |
| 2,487,859 | 11/1949 | Dickey et al. | 260/551 P |
| 2,750,399 | 6/1956 | Gamrath et al. | 260/974 |
| 2,960,527 | 11/1960 | Granze et al. | 260/940 |

OTHER PUBLICATIONS

Houben-Weyl, vol. 2, p. 212.

*Primary Examiner*—Anton H. Sutto
*Attorney, Agent, or Firm*—Sprung, Felfe, Horn, Lynch & Kramer

[57] ABSTRACT

In the preparation of a phosphoric acid alkyl ester dichloride by reacting phosphorus oxychloride with an aliphatic alcohol according to the equation

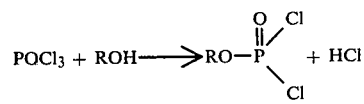

in which
R represents $C_1$–$C_5$-alkyl, the improvement which comprises carrying out the reaction continuously at a temperature of about 10° to 50° C. using an excess of phosphorus oxychloride of about 5 to 40%. The excess phosphorus oxychloride is reacted with the alcohol by continuous mixing, the reaction mixture is cooled, substantially all the hydrogen chloride formed is then separated off in a preliminary degassing stage, the reaction mixture is worked up in a distillation column, the unreacted phosphorus oxychloride and any diluent is separated off over the top and condensed, the condensate is recycled to the reaction and the corresponding alkyl ester dichloride is removed continuously as the bottom product.

7 Claims, 1 Drawing Figure

CONTINUOUS PREPARATION OF PHOSPHORIC ACID ALKYL ESTER DICHLORIDES

The invention relates to an unobvious process for the preparation of certain phosphoric acid alkyl ester dichlorides.

It is known that phosphoric acid alkyl ester dichlorides are obtained when phosphorus oxychloride is allowed to react with the corresponding alcohol in the presence of a solvent, for example carbon tetrachloride or petroleum ether (Compt. rend. 246, 1879 (1958); J. Am. Chem. Soc. 51, 953 (1929)). However, the yields of 60–70% are low, and they are decreased still further if the reaction temperatures are increased.

According to Houben-Weyl XII, 2, page 212, the following criteria are important for a good yield; low reaction temperatures (about ±0° C.), an excess of phosphorus oxychloride and as rapid as possible a removal of the hydrogen chloride formed. Only under these preconditions can the formation of phosphoric acid dialkyl ester chlorides, phosphoric acid trialkyl esters and alkyl chlorides be suppressed.

According to U.S. Pat. No. 2,487,859, carbon dioxide is bubbled through the reaction mixture to remove, at a rapid rate, the hydrogen chloride formed.

In Chemický průmysl, 11, 461 (1961), in addition to discontinuous reactions, semi-continuous reactions according to the equation

$$POCl_3 + CH_3OH \rightarrow CH_3O-P(O)Cl_2 + HCl$$

are also described. The reaction components are first heated to temperatures which are 10°–15° C. above the boiling point of the alcohol, and then mixed in a jet. In spite of the relatively good yields, this process is unsuitable for carrying out on an industrial scale because of the high energy consumption.

A continuous process has now been found for the preparation of phosphoric acid alkyl ester dichlorides, in which an excess of phosphorus oxychloride is reacted with the corresponding alcohol, a diluent being added if necessary.

The invention accordingly provides a process for the preparation of a phosphoric acid alkyl ester dichloride by reacting phosphorus oxychloride with an aliphatic alcohol according to the equation

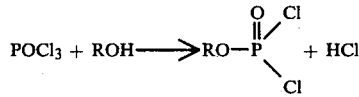

in which
R represents $C_1$–$C_5$-alkyl,
which process is characterized in that the reaction is carried out continuously at a temperature of about 10° to 50° using an excess of phosphorus oxychloride of about 5 to 400%.

An excess of phosphorus oxychloride is employed in the process according to the invention in order to largely suppress the formation of by-products. Although an excess of 5 to 400% can be used, an excess of between about 10 to 50% is preferred.

The process according to the invention is preferably carried out in the temperature range from about 20° C. to 40° C.

The process according to the invention can be carried out under reduced pressure, normal pressure or increased pressure, preferably under normal pressure.

The process according to the invention is preferably carried out continuously, in a reaction apparatus in which the residence time in the reaction mixture of the hydrogen chloride formed is only short.

Diluents which are to be used if necessary are, in general, solvents with approximately the same boiling point as phosphorus oxychloride; toluene is preferred.

The invention will be further described with reference to the accompanying drawing which is a flow sheet of a system for carrying out the instant continuous process.

Referring now more particularly to the drawing, phosphorus oxychloride (A), the alcohol (B) and if necessary a diluent (A') are mixed continuously in the mixing chamber (1). The reaction mixture is cooled in the cooler (2), and the hydrogen chloride formed is then separated off in a preliminary degassing stage (3) and passed on at (C) to an HCl absorption stage. At (C) there is also a connection to a vacuum pump. The reaction mixture, which is essentially free from HCl, is worked up in a distillation column (4); phosphorus oxychloride and the diluent used thereby pass over the top and are condensed in the condenser (5). The condensate is recycled into the reaction. The bottom product (D) from the distillation column (4) consists of the corresponding alkyl ester dichloride to the extent of about 95%. The yields are between 90 and 95%.

It is surprising that the phosphoric acid alkyl ester dichlorides are formed in such a high purity and yield in the process according to the invention, since it had to be expected, from the state of the art, that the yield would be drastically reduced at the relatively high reaction temperatures used.

The process according to the invention thus represents an enrichment of the art.

EXAMPLES

Phosphoric acid ethyl ester dichloride 148 kg/hour of phosphorus oxychloride, 148 kg/hour of toluene and 40 kg/hour of ethanol were mixed in the mixing chamber (1) of the apparatus illustrated in the drawing. The reaction mixture was kept at +20° C. by means of the cooler (2). The hydrogen chloride formed was removed in vacuo in the preliminary degassing stage (3) (T=60° C., P=100 mbars). In the column (4), 15 kg/hour of phosphorus oxychloride and 148 kg/hour of toluene were distilled off over the top, also in vacuo, and were recycled into the reaction. 141 kg/hour of a product having the following composition ran out at the bottom of the column: 95% of phosphoric acid ethyl ester dichloride, 3% of phosphoric acid diethyl ester chloride and 2% of unknown substances.

Phosphoric acid methyl ester dichloride

Phosphoric acid methyl ester dichloride could be prepared in the same manner, with an excess of phosphorus oxychloride of about 30%. In this case, the yields were 90%.

It will be appreciated that the instant specification and examples are set forth by way of illustration and not limitation, and that various modifications and changes may be made without departing from the spirit and scope of the present invention.

We claim:

1. In the preparation of a phosphoric acid alkyl ester dichloride by reacting phosphorus oxychloride with an aliphatic alcohol according to the equation $$POCl_3 + ROH \longrightarrow RO-\overset{\overset{O}{\|}}{P}\overset{Cl}{\underset{Cl}{\diagdown}} + HCl$$

in which
R represents $C_1$–$C_5$-alkyl,
the improvement which comprises carrying out the reaction continuously at a temperature of about 10° to 50° C. using an excess of phosphorus oxychloride of about 5 to 400%.

2. A process according to claim 1, wherein the excess phosphorus oxychloride is reacted with the alcohol by continuous mixing, the reaction mixture is cooled, substantially all the hydrogen chloride formed is then separated off in a preliminary degassing stage, the reaction mixture is worked up in a distillation column, the unreacted phosphorus oxychloride and any diluent is separated off over the top and condensed, the condensate is recycled to the reaction and the corresponding alkyl ester dichloride is removed continuously as the bottom product.

3. A process according to claim 1, wherein the excess of phosphorus oxychloride is from about 10 to 50%.

4. A process according to claim 1, wherein the reaction is effected at about 20° to 40° C.

5. A process according to claim 1, wherein toluene is used as a diluent.

6. A process according to claim 1, wherein R is methyl or ethyl.

7. A process according to claim 2, wherein R is methyl or ethyl, the excess of phosphorus oxychloride is from about 10 to 50%, the reaction is effected at about 20° to 40° C., and toluene is used as a diluent.

* * * * *